US012036293B2

(12) United States Patent
Blower et al.

(10) Patent No.: US 12,036,293 B2
(45) Date of Patent: *Jul. 16, 2024

(54) METHODS AND KITS FOR PREPARING RADIONUCLIDE COMPLEXES

(71) Applicant: THERAGNOSTICS LIMITED, London (GB)

(72) Inventors: Philip Blower, London (GB); Gregory Mullen, Reading (GB)

(*) Notice: Subject to any disclaimer, the term of this patent is extended or adjusted under 35 U.S.C. 154(b) by 579 days.

This patent is subject to a terminal disclaimer.

(21) Appl. No.: 17/154,926

(22) Filed: Jan. 21, 2021

(65) Prior Publication Data

US 2021/0138094 A1    May 13, 2021

Related U.S. Application Data

(63) Continuation of application No. 15/554,573, filed as application No. PCT/GB2016/050637 on Mar. 9, 2016, now abandoned.

(30) Foreign Application Priority Data

Mar. 10, 2015  (GB) .................................... 1504064

(51) Int. Cl.
| | | |
|---|---|---|
| A61K 51/04 | (2006.01) | |
| A61B 5/00 | (2006.01) | |
| A61K 51/08 | (2006.01) | |
| A61P 35/00 | (2006.01) | |
| C01G 15/00 | (2006.01) | |
| C07B 59/00 | (2006.01) | |
| C07C 251/24 | (2006.01) | |
| C07F 5/00 | (2006.01) | |

(52) U.S. Cl.
CPC ........ *A61K 51/0478* (2013.01); *A61B 5/0035* (2013.01); *A61K 51/082* (2013.01); *A61K 51/088* (2013.01); *A61P 35/00* (2018.01); *C01G 15/00* (2013.01); *C07B 59/00* (2013.01); *C07C 251/24* (2013.01); *C07F 5/00* (2013.01)

(58) Field of Classification Search
CPC .......... A61K 51/04; A61K 51/08; A61P 35/00
See application file for complete search history.

(56) References Cited

U.S. PATENT DOCUMENTS

| | | |
|---|---|---|
| 4,330,507 A | 5/1982 | Lewis |
| 7,011,816 B2 | 3/2006 | Griffiths et al. |
| 8,663,597 B2 | 3/2014 | Ulin et al. |
| 2003/0176784 A1 | 9/2003 | Griffiths et al. |
| 2013/0310537 A1 | 11/2013 | Muller |
| 2014/0171637 A1* | 6/2014 | Fugazza .................. C07B 59/00 540/465 |
| 2015/0133634 A1 | 5/2015 | Muller |

FOREIGN PATENT DOCUMENTS

| | | |
|---|---|---|
| BE | 1021191 B1 * 10/2015 | ............. A61K 51/04 |
| BE | 1021191 B1 | 10/2015 |
| CA | 2113995 C | 3/1993 |
| EP | 2 444 800 A2 | 4/2012 |
| EP | 3 064 224 A1 | 9/2016 |
| JP | H6-510539 A | 11/1994 |
| JP | 2014-501714 A | 1/2014 |
| JP | 2014-524423 A | 9/2014 |
| JP | 2017-526745 A | 9/2017 |
| JP | 6889665 B2 | 6/2021 |
| JP | 7109627 B2 | 7/2022 |
| WO | 93/04702 A1 | 3/1993 |
| WO | 03/059397 A2 | 7/2003 |
| WO | 2009/021947 A1 | 2/2009 |
| WO | 2010/087959 A1 | 8/2010 |
| WO | 2011/098611 A2 | 8/2011 |
| WO | 2012/063028 A1 | 5/2012 |
| WO | 2013/024013 A2 | 2/2013 |
| WO | 2014/178229 A1 | 11/2014 |
| WO | 2015/106025 A1 | 7/2015 |
| WO | 2016/030103 A1 | 3/2016 |
| WO | 2016/030104 A1 | 3/2016 |
| WO | 2016/142702 A1 | 9/2016 |

OTHER PUBLICATIONS

Eder et al.68Ga-Complex Lipophilicity and theTargeting Property of a Urea-Based PSMA Inhibitor for PET imaging, Bioconjugate Chemistry, 23,688-697. (Year: 2012).*
Office Action mailed Oct. 13, 2022 in U.S. Appl. No. 17/857,990, 22 pgs.
"Arginine," description from Wikipedia, last edited Jun. 27, 2021, retrieved from https://en.wikipedia.org/w/index.php?title=Arginine &oldid=1030736961, 12 pages.
Ebenhan et al., "Development of a Single Vial Kit Solution for Radiolabeling of 68Ga-DKFZ-PSMA-11 and Its Performance in Prostate Cancer Patients," Molecules, 2015, pp. 14860-14878, vol. 20.
Golan et al., "Enhancing capacity and synthesis of [68Ga]68-Ga-PSMA-HBED-CC with the lyophilized ready-to-use kit for nuclear pharmacy applications," Nuclear Medicine Communications, 2020, pp. 986-990, vol. 41, No. 9.

(Continued)

*Primary Examiner* — Michael G. Hartley
*Assistant Examiner* — Jagadishwar R Samala
(74) *Attorney, Agent, or Firm* — Polsinelli PC; Tara A. Nealey

(57) ABSTRACT

A method for preparing a complex comprising a radioisotope of gallium for use in radiotherapy or in a medical imaging procedure, said method comprising adding a gallium radioisotope solution obtained directly from a gallium radionuclide generator to a composition comprising a pharmaceutically acceptable buffer and optionally also a pharmaceutically acceptable basic reagent, in amounts sufficient to increase the pH to a level in the range of 3 to 8, wherein the composition further comprises a chelator that is able to chelate radioactive gallium within said pH range and at moderate temperature, said chelator being optionally linked to a biological targeting agent. Kits and compositions for use in the method are also described and claimed.

7 Claims, 1 Drawing Sheet

(56) References Cited

OTHER PUBLICATIONS

Ma et al., "Extremely rapid, kit-based biomolecule labelling and molecular imaging with gallium-68: tris (hydroxypyridinone) chelators," Abstract, Chapter in Book/Report/Conference proceeding, 28th Annual Congress of the European-Association-of-Nuclear-Medicine (EANM), pp. S198-S199, vol. 42, published Oct. 2015.

Ma et al., "Rapid kit-based 68Ga-labelling and PET imaging with THP-Tyr3-octreotate: a preliminary comparison with DOTA-Tyr3-octreotate," EJNMMI Research, 2015, 11 pgs., vol. 5, No. 52.

Roesch et al., "The Renaissance of the 68Ge/68Ga Radionuclide Generator Initiates New Developments in 68Ga Radiopharmaceutical Chemistry," Current Topics in Medicinal Chemistry, 2010, pp. 1633-1668, vol. 10, No. 16.

Notice of Opposition filed against European Patent No. 3268337 in the European Patent Office on Dec. 22, 2020, in the name and on behalf of Dehmel & Bettenhausen; 40 pages.

Response to Notice of Opposition against European Patent No. 3268337, filed by Theragnostics Limited in the European Patent Office on Oct. 4, 2021; 17 pages.

Office Action mailed Mar. 3, 2023 in U.S. Appl. No. 17/858,990, 12 pages.

Baheti et al., "Excipients used in lyophilization of small molecules," J. Excipients and Food Chem., 2010, pp. 41-54, vol. 1, No. 1.

Berry et al., "Efficient bifunctional gallium-68 chelators for positron emission tomography: tris(hydroxypyridinone) ligands," Chem Commun (Camb), 2011, pp. 7068-7070, vol. 47, No. 25.

Breeman et al., "Radiolabelling DOTA-peptides with 68Ga," European Journal of Nuclear Medicine and Molecular Imaging, 2005, pp. 478-485, vol. 32, No. 4.

Eder et al., "68Ga-Complex Lipophilicity and the Targeting Property of a Urea-Based PSMA Inhibitor for PET Imaging," Bioconjugate Chemistry, 2012, pp. 688-697, vol. 23.

Emberson et al., "Expression of an anti-CD33 single-chain antibody by Pichia pastoris," Journal of Immunological Methods, 2005, pp. 135-151, vol. 305.

Giersing et al., "Synthesis and Characterization of 111 In-DTPA-N-TIMP-2: A Radiopharmaceutical for Imaging Matrix Metalloproteinase Expression," Bioconjugate Chemistry, 2001, pp. 964-971, vol. 12, No. 6.

International Search Report and Written Opinion from International Application No. PCT/GB2016/050637, dated May 27, 2016; 10 pgs.

Munch et al., "A new efficient synthesis of isothiocyanates from amines using di-tert-butyl dicarbonate," Tetrahedron Letters, 2008, pp. 3117-3119, vol. 49.

Zhou et al., "Iron Binding Dendrimers: A Novel Approach for the Treatment of Haemochromatosis," Journal of Medicinal Chemistry, 2006, pp. 4171-4182, vol. 49, No. 14.

Japanese Office Action from Japanese Application No. 2017-566214, dated Jan. 23, 2020; 7 pgs.

Martiniova et al., "Gallium-68 in Medical Imaging," Current Radiopharmaceuticals, 2016, pp. 187-207, vol. 9, No. 3.

Simecek et al., "Benefits of NOPO as Chelator in Gallium-68 Peptides, Exemplified by Preclinical Characterization of 68Ga-NOPO-c(RGDfK), " Molecular Pharmaceutics, 2014, pp. 1687-1695, vol. 11.

Notice of Reasons for Refusal for related Japanese Patent Application No. 2022-114907, received Aug. 29, 2023, 4 pages.

Appeal filed by Dehmel & Bettenhausen Patentanwalte PartmbB Against the Opposition Division Decision in respect of European Patent No. 3268337 B1, dated Mar. 21, 2023, 28 pages.

Appeal filed by Dehmel & Bettenhausen Patentanwalte PartmbB Against the Opposition Division Decision in respect of European Patent No. 3268337 B1, dated Aug. 7, 2023, 10 pages.

Eckert et al., "Eckert and Ziegler GalliaPharm TM Germanium-68/Gallium-68 Pharmacy Grade Generator Licensing Guidance", 2016, 13 pages.

Eder et al., "Tetrafluorophenolate of HBED-CC: a versatile conjugation agent for 68Ga-labeled small recombinant antibodies", European journal of nuclear medicine and molecular imaging, 2008, pp. 1878-1886, vol. 35,10.

Grounds of Appeal in European Patent Application No. 16712997.2, dated Mar. 21, 2023, 10 pages.

Hammerstein et al., "Single-Molecule Kinetics of Two-Step Divalent Cation Chelation", Angew. Chem. Int. Ed., 2010, pp. 5085-5090, vol. 49.

Imberti et al., "Tuning the properties of tris(hydroxypyridinone) ligands: efficient 68Ga chelators for PET imaging", Dalton transactions (Cambridge, England : 2003), 2019, pp. 4299-4313, vol. 48,13.

Ogawa et al., "Advances in Drug Design of Radiometal-Based Imaging Agents for Bone Disorders", International Journal of Molecular Imaging, 2011, 7 pages, vol. 2011, Article ID 537687, Hindawi Publishing Corporation.

Reply to the Opponent's Grounds of Appeal in European Patent Application No. 16712997.2, dated Aug. 7, 2023, 10 pages.

Schuhmacher et al., "A Bifunctional HBED-derivative for Labeling of Antibodies with 67 Ga, 111 In and 59 Fe. Comparative Biodistribution with 111 In-DPTA and 131 1-labeled Antibodies in Mice Bearing Antibody Internalizing and Non-internalizing Tumors", Nucl. Med. Biol., 1992, pp. 809-824, vol. 19, No. 8.

Schwartzbach, "Achieving aseptic drying with spray drying technologies", Pharmaceutical Technology Europe, 2011, pp. 90-92, Advanstar Communications Inc.

Taliaferro et al., "New Multidentate Ligands. XXIV. Disodium-N ,N'-bis(2-hydroxy-S-sulfobenzyl )-ethylenediaminediacetic Acid, a New Chelating Ligand for Trivalent Metal Ions", Inorganica Chimica Acta, 1984, pp. 9-15, vol. 85.

Velikyan, "Prospective of 68Ga-Radiopharmaceutical Development", Theranostics, 2014, pp. 47-80, vol. 4, Issue 1.

"BP2021 (Ph. Eur. 10.4 update)—Search Results", British Pharmacopoeia, 2020, 3 pages.

"Chelation", Wikipedia, the free encyclopedia, last modified Feb. 10, 2015, 7 pages, retrieved from http://en.wikipedia.org/w/index.php?title=Chelation&oldid=646498670.

"Gallium (68Ga) PSMA-11 Injection", European Pharmacopoeia 10.4, pp. 5397-5398.

Non-Final Office Action from related U.S. Appl. No. 17/857,990 dated Aug. 16, 2023, 11 pages.

Notice of Allowance from related U.S. Appl. No. 17/857,990 dated Oct. 17, 2023, 17 pages.

Non-final Office Action for related U.S. Appl. No. 18/499,758, dated Mar. 27, 2024, 17 pages.

Afshar-Oromich, et al., "The diagnostic value of PET/CT imaging with the 68Ga-labelled PSMA ligand HBED-CC in the diagnosis of recurrent prostate cancer", Eur J Nucl Med Mol Imaging, 2015, pp. 197-209, vol. 42.

* cited by examiner

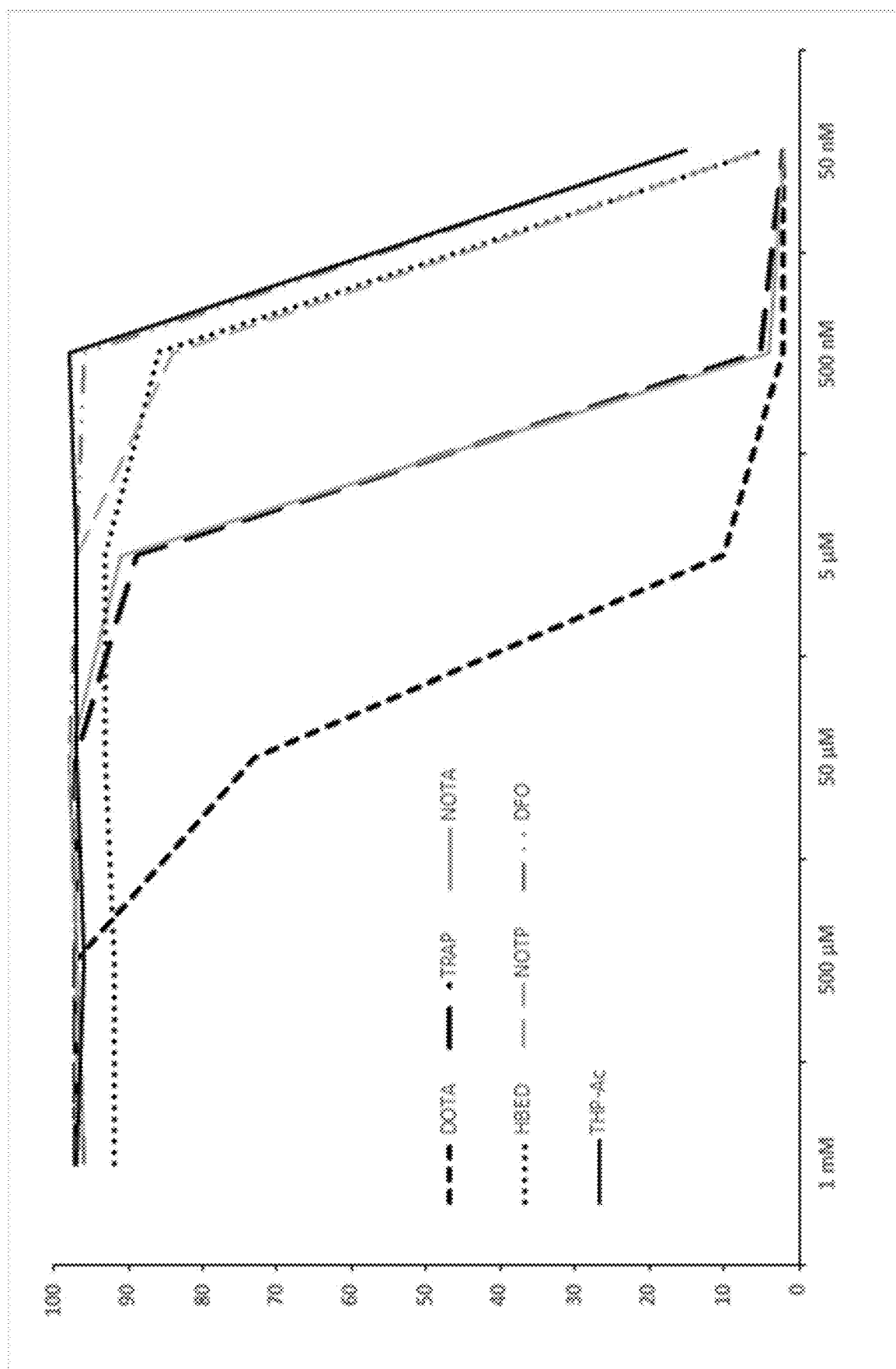

METHODS AND KITS FOR PREPARING RADIONUCLIDE COMPLEXES

CROSS-REFERENCE TO RELATED APPLICATIONS

This application is a continuation of U.S. patent application Ser. No. 15/554,573, filed Aug. 30, 2017, which is a U.S. National Stage Application of International Patent Application No. PCT/GB2016/050637, filed Mar. 9, 2016, which claims the benefit of, and priority to Great Britain Patent Application No. 1504064.5, filed Mar. 10, 2015, the entire contents of which are hereby incorporated by reference in their entirety.

FIELD OF THE INVENTION

The present invention relates to methods for preparing radioactive gallium complexes for use in therapy or diagnosis, for example in molecular imaging procedures, to kits for use in these methods, and to novel compositions used in them as well as to methods for molecular imaging and therapy carried out using the compositions or the kits.

BACKGROUND TO THE INVENTION

Molecular imaging is a well-known and useful technique for in vivo diagnostics. It may be used in a wide variety of methods including the three-dimensional mapping of molecular processes, such as gene expression, blood flow, physiological changes (pH, etc.), immune responses and cell trafficking. It can be used to detect and diagnose disease, select optimal treatments, and to monitor the effects of treatments to obtain an early readout of efficacy.

A number of distinct technologies can in principle be used for molecular imaging, including positron emission tomography (PET), single photon emission tomography (SPET), optical (OI) magnetic resonance imaging (MRI), X-ray Computed Tomography (CT) and Cerenkov luminescence imaging (CLI). Combinations of these modalities are emerging to provide improved clinical applications, e.g. PET/CT and SPET/CT ("multi-modal imaging").

Radionuclide imaging with PET and SPET has the advantage of extremely high sensitivity and small amounts of administered contrast agents (e.g. picomolar in vivo), which do not perturb the in vivo molecular processes. Moreover, the targeting principles for radionuclide imaging can be applied also in targeted delivery of radionuclide therapy. Typically the isotope that is used as a radionuclide in molecular imaging or therapy is incorporated into a molecule to produce a radiotracer that is pharmaceutically acceptable to the subject.

Most radiotracers have a relatively short half-life and so have to be produced in situ, for example in the radiopharmacy section of the relevant hospital, under sterile conditions. Some hospitals have difficulty with this if they do not have specialist radiochemistry laboratories and therefore their ability to offer treatments such as PET may be restricted.

It may be difficult to prepare radiotracers with sensitive functional moieties. For example, incorporation of radioisotopes into the radiotracer may involve elevated temperatures that would disrupt protein structure and add undesirable complexity to the labelling process. It may be desirable to include sensitive functional moieties into radiotracers and so it is a need to provide radiotracers that may be prepared using mild conditions. Moreover it is desirable that labelling processes at the point of use are as simple as possible, with the minimum number of manipulations of radioactive materials, minimal need for costly equipment to perform the manipulations and the shortest possible time of preparation. As a result imaging conjugates with improved functionality and improved molecular imaging properties have been produced.

1,4,7, 10-tetraazacyclododecane-N,N',N'',N'''-tetraacetic acid (DOTA) is a common chelator for gallium-68 (and other metallic radioisotopes such as Ga-67, In-111, Cu-64, Lu-177, Y-90) used in molecular imaging and targeted radionuclide therapy. However, DOTA has a long radiolabelling time of around 30 to 60 minutes (relative to the half-life of $^{68}$Ga~68 minutes), which reduces the useful life of the tracer. In addition, chelation of gallium by DOTA derivatives often requires a high labelling temperature of around 95° C. and acidic pH, which may be damaging to any biological targeting agent associated with the biotracer and adds complexity to the process.

WO2012/063028 describes a range of bifunctional molecules that are able to quickly chelate radionuclides at room temperature, whilst retaining stability towards dissociation in the biological milieu. In addition to the metal chelating portion, the bifunctional molecules have a reactive portion to couple the bifunctional molecule to a functional moiety, such as targeting group which can target, for example, cells, tissues or biological molecules in the body. They chelate at neutral pHs. Kits comprising these bifunctional molecules and radionuclides are also described.

However, a residual problem arises in relation to the radionuclides themselves. These are generally obtained by elution from generators. Many of these isotopes, such as $^{68}$Ga will only elute at low pH, for example at a pH of less than 2, such as about 1. At present, they require complex pretreatment procedures to raise the pH prior to or after addition to the chelator to produce a radiotracer. In particular, gallium is liable to precipitate out of solution at neutral to high pH and so requires particular handling. Typically, an eluate from a $^{68}$Ga generator for instance, is first subject to a purification step by passage through a cation exchange cartridge before it may be contacted with the chelator. In many cases, the labelling procedure is also complex. For example, it may be necessary to add buffer and acid with the chelating compound and then heat the mixture to relatively high temperatures, for example of 100° C., to achieve labelling. Then the product may require passing through further purification cartridges such as a SEP-Pak C-18 cartridge before being diluted in phosphate buffered saline (PBS) solution and passed through a sterile filter. All this requires complex and dedicated apparatus and the time taken erodes the useful life of the radionuclide.

WO2012/063028 describes that $^{68}$Ga eluate must be further acidified, and passed down an anion exchange column to concentrate it, before it is buffered and added to the bifunctional molecule to form the radiotracer. Such procedures require skilled staff and complex equipment which is not always available. They must be carried out in a strictly sterile environment. In addition, $^{67}$Ga radiolabelling was carried out by first reacting $^{67}$Ga citrate (which is of acidic pH), with the chelator complex followed by a subsequent buffering step, which again involves two steps.

So-called 'cold kits' have been produced previously for use with Technetium radiolabels. These are relatively simple to use and do not require significant handling of the radionuclide. However, in contrast to $^{68}$Ga, technetium is obtainable directly from a generator at close to neutral pH, typically of the order of from 4 to 8, and usually about 7.

The applicants have developed a method in which certain types of radionuclide chelator groups which may optionally be attached to targeting groups, can be formulated in a manner that allows them to be utilised directly with gallium solutions such as radionuclide eluates, in particular either those at low pH or neutral pH. As a result, the compositions can be used to provide robust, versatile and easy to use 'kits' that may be employed in clinical situations such as in hospitals.

SUMMARY OF THE INVENTION

According to a first aspect of the invention there is provided a method for preparing a complex comprising a radioisotope of gallium for use in radiotherapy or in a medical imaging procedure, said method comprising adding a gallium radioisotope solution obtained directly from a gallium generator to a composition comprising a pharmaceutically acceptable buffer and optionally also a pharmaceutically acceptable basic reagent, in amounts sufficient to increase the pH to a level in the range of 3 to 8, wherein the composition further comprises a chelator that is able to chelate radioactive gallium within said pH range and at moderate temperature, said chelator being optionally linked to a biological targeting agent.

The applicants have found that effective gallium radiolabelling may be achieved directly by contact with gallium solutions, in particular acidic solutions including the highly acidic eluates obtainable from $^{68}$Ga radionuclide generators which are generally at a pH of less than 2, for example at a pH of 1. No undue gallium precipitation occurs. As a result, gallium labelling procedures may be simplified by avoiding additional steps such as purification or concentration steps using ion exchange columns or membranes for example. In a particular embodiment, when the gallium radioisotope solution is $^{68}$Ga solution from a generator, there will be no need to subject it to an initial concentration step and no need to pass the solution through an ion exchange medium.

Suitable gallium-68 generators that may be used to supply the gallium radioisotope solution include Eckert & Ziegler's *GalliaPharm* 9, IRE-Elite Galli Eo™ and Parsisotope GalluGEN.

The method is also applicable to solutions of $^{67}$Ga salts, such as gallium citrate, which may be produced from a cyclotron. The resultant radiolabelled product may be of sufficiently high purity that it may be used directly in medical procedures such as radiotherapy or molecular imaging. In this instance, the product of the cyclotron is 'a gallium radioisotope solution obtained directly from a gallium generator' as required by the method of the invention.

The acidic solution such as the eluate is added to a composition comprising both the pharmaceutically acceptable buffer and the chelator and also a pharmaceutically acceptable basic reagent if required or necessary. As used herein, the term 'basic reagent' refers to a compound that will produce a neutralising effect when contacted with an acidic material.

Thus, the chelator is present in the composition comprising the pharmaceutically acceptable buffer and the pharmaceutically acceptable basic reagent as a 'pre-mix'. This provides an efficient 'single step' procedure, in which the acidic gallium solution is added directly to the pre-mix composition so that the chelation and neutralisation occurs simultaneously.

The chelator for the radionuclide may be any chelator which is effective at moderate temperatures, for example from 10-30° C., and suitably at ambient temperature, and at moderate pHs, for example of from 3-8 and at low concentrations (for example from 1-1004) and reaching acceptable yield in a short time (e.g. 1-5 minutes). In this instance, acceptable yields of complex would be at least 60%, for instance at least 70%, 80%, 90% or 95% of the administered radiolabel.

The chelation may be achieved at moderate temperatures and in particular at ambient temperature, so that heating steps or stages may be avoided, thus simplifying the procedure and ensuring that the radioactivity of the gallium remains at a good level. Versatile chelators of this type, which are effective at neutral pHs as well as at low pH, are known in the art.

For example, suitable chelators include HBED, DFO, DTPA, DOTA, TRAP, NOTA, NOPO, NODAGA, MPO, 6SS, B6SS, PLED, TAME, NTP, and BAPEN.

In particular the radionuclide chelator is a compound of formula (I)

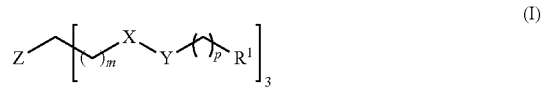

or a salt thereof; wherein one of X and Y is C=O and the other is NR; wherein each m and p are independently selected from 0 to 6; wherein R$^1$ is a chelating group capable of chelating a radionuclide and is selected from:

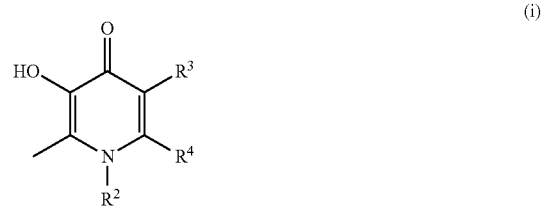

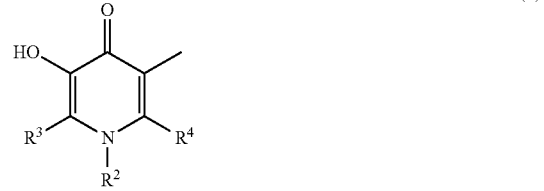

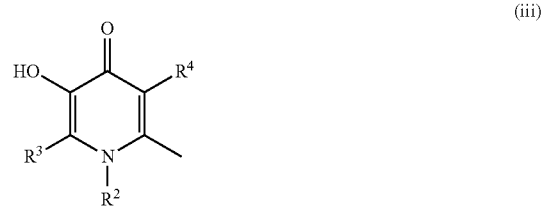

wherein R, R$^2$, R$^3$ and R$^4$ are independently hydrogen or an optionally substituted C$_{1-7}$alkyl group;
and where Z is hydrogen or a group of formula —B'—H, —B'-A, or a group —B'-A*-T, where
T is a targeting group capable of binding to a target of interest in a subject;
A is a reactive group allowing coupling to the group T,
A* is a reacted reactive group A;
B' is a linker group for linking the chelating group to a reactive group A, and is represented by the formula:

wherein each Q is independently selected from a group consisting of —NR$^5$—, —C(O)NR$^5$—, —C(O)O, —NR$^5$C(O)NR$^5$—, —NR$^5$C(S)NR$^5$— and —O—, each R$^5$ is independently hydrogen or an optionally substituted C$_{1-7}$ alkyl group, each q and s are independently selected from 0 to 6 and each r is independently selected from 1 to 6.

Chelators of formula (I) are able to chelate radionuclides such as gallium radionuclides at a pH in the range of from 3 to 8 with a very high efficiency and at moderate temperature in a short time at low concentration. Chelators of this general type provide a useful advance over many of the previously known chelators, which only worked at low pH and therefore resulted in compositions which were not well suited to pharmaceutical application. By combining a chelator of this type with a neutralising alkaline salt and a buffer ab initio, in particular in a single unitary composition, the applicants have found that the composition may be used directly with gallium solutions having a range of acidic pHs, such as a solution of a $^{67}$Ga salt, for instance $^{67}$Ga citrate, obtainable from a cyclotron, as well as an eluate from a $^{68}$Ga radionuclide generator, even when this is at low pH, for example of 2 or less, without requiring complex preparation or purification steps. This simplifies the production process and allows the possibility of forming 'cold kits' for use with specifically gallium radionuclides with minimal manipulation.

In a particular embodiment, the reagents used in the method (chelator, buffer and basic reagent) are in solid form, in particular in lyophilized or freeze-dried form. This allows them to form a stable mixture that may be stored or transported ready for use for generating radiotracers in situ. In one embodiment, the buffer and basic components are contained in one vessel or vial, to which an eluate from a gallium radionuclide generator may be added. The contents of this vial may then be simply added to a second vial or vessel containing the solid chelator. In another particular embodiment, all the reagents are combined in a single unitary composition. Suitably, the unitary composition is divided into units containing sufficient chelator for a single imaging operation. In this instance the generator may be eluted directly into the container such as the vial holding the unitary composition.

The amount of pharmaceutically acceptable buffer and, where necessary, any basic reagent, used in the method should be suitable for raising and maintaining the pH of the mixture formed on addition of the acidic gallium solution, such as the eluate from a $^{68}$Ga radionuclide generator to a pharmaceutically acceptable level, for example, in the range of from 3-8, for example from 4-7 such as from 5.5-7 and in particular from 6.5-7.5 or pH 6.0 to 7.0 on reconstitution, as well as maintaining a level at which the chelator will be effective to chelate a gallium radionuclide. The applicants have found that, under these circumstances, the activity of the chelator is not significantly reduced by direct exposure to low pHs. Furthermore, no unwanted precipitation of gallium occurs as a result of exposure to high pH, which is a problem that has been encountered previously in connection when handling specifically gallium solutions. Compositions in this pH range may be administered to patients directly without undue pain caused by high acidity.

The amount of chelator used in the method and so present in the composition will vary depending upon factors such as the precise nature of the chelator, the nature of the radionuclide to be chelated as well as the nature of the therapy or imaging process being undertaken. However, typically, the amount of chelator required in a composition for carrying out a single therapeutic treatment or imaging procedure is in the range of from 0.1-10 µmoles. In a liquid composition, for example, one produced for lyophilisation to form a solid composition or after reconstitution for administration, the concentration of the chelator is suitably in excess of 5 µM, for example, from 10-100 µM.

Suitable pharmaceutically acceptable buffers include inorganic and organic buffers. Examples of inorganic buffers include phosphate buffers, such as sodium phosphate, sodium phosphate dibasic, potassium phosphate and ammonium phosphate; bicarbonate or carbonate buffers; succinate buffers such as disodium succinate hexahydrate; borate buffers such as sodium borate; cacodylate buffers; citrate buffers such as sodium citrate or potassium citrate; sodium chloride, zinc chloride or zwitterionic buffers. Examples of organic buffers include tris(hydroxymethyl)aminomethane (TRIS) buffers, such as Tris HCl, Tris EDTA, Tris Acetate, Tris phosphate or Tris glycine, morpholine propanesulphonic acid (MOPS), and N-(2-hydroxyethyl) piperazine-N' (2-ethanesulfonic acid) (HEPES), dextrose, lactose, tartaric acid, arginine or acetate buffers such as ammonium, sodium or potassium acetate. In a particular embodiment, the buffer is other than an acetate buffer, and other than a sodium acetate buffer.

Suitably the buffer is a phosphate buffer, such as sodium phosphate buffer. The buffer may comprise one or more phosphate salt, and in particular comprise a monobasic and dibasic sodium phosphate salt. For example, a suitable buffer comprises sodium phosphate monobasic anhydrous and sodium phosphate dibasic heptahydrate in a ratio of about 1.5:1 to 2.5:1.

The total amount of buffer present will depend upon factors such as the particular nature of the buffer and the nature of the complex as well as the particular molecular imaging procedure which is to be carried out. Typically however, the buffer is present in the dried composition in an amount of from 5 to 95 mole percent. Thus, in a liquid composition, for example, one produced for lyophilisation to form a solid composition or after reconstitution for administration, the concentration of the buffer reagent is suitably in the range of from 0.01 to 0.6M, for example from 0.1 to 0.5M, for example at about 0.2M (20 mM).

In some embodiments, it may not be necessary to include a pharmaceutically acceptable basic reagent, in particular where the buffer is a particularly 'strong' buffer such as ammonium acetate. However, in a particular embodiment, a pharmaceutically acceptable basic reagent is added to the buffer to facilitate neutralisation of the eluate. Suitable pharmaceutically acceptable basic reagents include alkaline salts such as hydroxides, carbonates, bicarbonates or oxides of alkali or alkaline earth metals, such as sodium, potassium, calcium or magnesium, or ammonium salts or basic organic reagents. For example, suitable reagents may be selected from sodium hydroxide, potassium hydroxide, ammonium hydroxide, magnesium oxide, calcium carbonate, magnesium carbonate, magnesium aluminum silicates, sodium carbonate, sodium bicarbonate, triethanolamine, or any combination thereof, In particular, the pharmaceutically acceptable basic reagent is an alkali metal salt, such as an alkali metal hydroxide, in particular sodium or potassium hydroxide. In an alternative embodiment, the basic reagent is sodium bicarbonate.

The amount of pharmaceutically acceptable basic reagent present in the composition will vary depending upon factors such as the precise nature of the reagent, the intended use of the kit and thus the pH of the eluate of the particular radionuclide generator intended to be used with it. Typically however, the amount of such reagent in a composition for use in a single therapy or imaging operation is from 0.5-0.75 mmoles. Thus, in a liquid composition, for example, one produced for lyophilisation to form a solid composition or after reconstitution for administration, the concentration of the basic reagent is suitably in the range of from 0.01 to 0.6M, for example from 0.1 to 0.15M.

In a particular embodiment, the chelator of formula (I) is, or has the capability of becoming linked to a targeting moiety T as defined above.

The complexes used in the compositions of the invention will suitably comprise a biological targeting agent that is bound to the chelator, in particular covalently as described above where the compound of formula (I) includes a group 'T', but otherwise, a biological targeting agent may be associated with the compound of formula (I) by other means, for example by conjugation. In particular the biological targeting agent is covalently bonded to the chelator and the chelator is a compound of formula (II) where Z is a group —B'-A*-T:

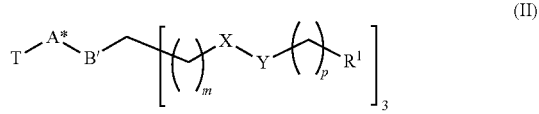

or a salt thereof; wherein T, A*, B', X, Y, R¹, m and p are as defined above.

In another embodiment, the chelator is a compound which is capable of reacting a targeting group, and therefore is a compound of formula (III)

or a salt thereof; wherein T, A, B', X, Y, R¹, m and p are as defined above.

Particularly preferred examples of compounds of formula (I) are described in WO2012/063028.

In a particular embodiment, R¹ is a group of sub-formula (i) or (ii) as described above, such as a group of sub-formula (i).

Suitably R³ and R⁴ are selected from hydrogen or lower $C_{1-4}$alkyl groups such as methyl. In a particular embodiment R³ is hydrogen. In another particular embodiment, R⁴ is methyl.

In a particular embodiment, each X, Y, m, p, Q, s, r and q are similar.

In a particular embodiment, X is C(O) and Y is NR. Suitably R is hydrogen or $C_{1-4}$alkyl and in particular is hydrogen.

In a particular embodiment, p is 1. In another particular embodiment, m is 2.

In a particular embodiment, q is 0.

Suitably, within the group B, Q is a group —C(O)NR⁵. In particular R⁵ is selected from hydrogen and $C_{1-4}$alkyl group, such as hydrogen.

Suitable biological targeting moieties T in formula (I) for use in the compositions of the invention will be groups which are capable of directing the molecules to different targets of interest in the biological system in question. Generally, these will therefore form a 'specific binding pair' with the target of interest, such that the targeting moiety T and the target of interest will have particular specificity for each other and which in normal conditions bind to each other in preference to binding to other molecules. Examples of specific binding pairs are well known in the art and include for example receptors and ligands, enzymes and substrates, and immunoglobulins such as antibodies and antigens. Thus, targeting moieties T may be peptides, proteins or other biological molecules, such as aptamers, or small molecule ligands, that bind to specific in vivo molecular targets. Classes of targets of interest include ligands or receptors or transporters expressed on diseased cells or tissue, cell surface antigen associated with disease states, or tumour markers, e.g. cancer specific markers or tissue specific markers.

In a particular embodiment, the targeting moiety T is a ligand that targets a cancer specific marker such as prostate specific membrane antigen (PSMA). Such ligands include DKFZ-PSMA-11 (Eder M. et al., Bioconjugate Chem. 2012, 688).

Alternatively, the targeting moiety T may comprise an antibody such as an anti-CD33 antibody, or binding fragment thereof, for imaging cancer cells expressing CD33 such as cells of myelomonocytic lineage and leukaemic cells, (see Emberson et al., J. Immunol. Methods. 305 (2): 135-51, 2005) or antibodies capable of binding to the glycoprotein carcinoembryonic antigen (CEA) as members of this family of glycoproteins are expressed on colorectal cancer cells, gastric cancer cells, pancreatic cancer cells, lung cancer cells, medullary thyroid cancer cells and breast cancer cells, as well as anti-PSMA antibodies and binding fragments thereof. Other suitable antibodies may show affinity to cell adhesion molecules. These include the monoclonal antibody, SER 4, which binds to the macrophage adhesion molecule, sialoadhesin. Sialoadhesin is found on the surface of macrophages, and, for example, in high amounts on macrophages of the spleen, liver, lymph node, bone marrow colon and lungs.

A further example of the suitable T groups are tissue inhibitors of metalloproteinases (TIMPs), such as TIMP-2, which allow for imaging matrix metalloproteinase expression, as expression of metalloproteinases has been implicated in metastatic processes, (see Giersing et al., Bioconjug Chem. 12(6): 964-71, 2001). In yet a further embodiment, the targeting moiety T may be a polypeptide such as complement receptor 2 (CR2). Yet a further example may exploit the affinity or the peptide sequence arginine-glycine-aspartic acid (RGD) for the [alpha][nu][beta]3 integrin expressed highly in the endothelium of tissues undergoing angiogenesis as is commonly seen in tumours, atherosclerotic plaque and repairing diseased tissue such as infarcted myocardium, by linking an RGD peptide derivative to the bifunctional compound by means of a suitable reactive group A. Other T groups may comprise the peptide octreotide or related analogues of somatostatin that have affinity to the somatostatin receptor expressed highly at the surface of cancer cells e.g. in carcinoid, medullary thyroid carcinoma and other neuroendocrine tumours.

In another embodiment, the targeting groups T are polypeptides capable of binding to phosphatidylserine (PS) so that the resultant complex can be employed in apoptosis or cell death imaging studies. Examples of such polypeptides include Annexin V and the C2 domain of a synaptotagmin. Polypeptides that comprise one or more C2 domains are well known in the art. While some polypeptides have only one C2 domain, others have two or more C2 domains, and the domains are generally described by attaching a letter (in alphabetical order) to the end of the name (e.g., C2A, C2B, and so on). For a protein that contains only one C2 domain, the domain is simply referred to as C2 domain. Particular examples include the C2A domain of rat synaptotagmin I or a C2A domain of a synaptotagmin of another species. Further examples of proteins that contain a C2 domain include but are not limited to synaptotagmin 1-13, protein kinase C family members of serine/threonine kinases, phospholipase A2, phospholipase 51, cofactors in the coagulation cascade including factors V and VIII, and members of the copine family. Human synaptotagmins include synaptotagmin 1-7, 12 and 13.

Other suitable targeting moieties T are bombesin, gastrin, or VCAM targeting peptide.

The targeting moieties T are linked to a chelator molecule to form the compound of formula (I) by means of a suitable linker group A*. The nature of the linker group A* will depend upon the nature of the targeting moiety T and will be determined using conventional chemistry.

Alternatively, they may comprise calcium chelating groups such as bisphosphonate derivatives, which target bones and in particular bone cancers.

In an alternative embodiment, the chelator may not include a targeting group, but act simply as a metal chelator, for general radiochemical monitoring, such as in monitoring of renal function.

Typically the linker group A* is formed from a reactive group A which, in a particular embodiment is a protein-reactive functional group. The protein reactive group may react with proteins or modified proteins or peptides or other vehicles derivatised for the purpose. Preferably the protein-reactive group A is or comprises a maleimide group, an isothiocyanate group such as an alkyl or arylisothiocyanate, an aldehyde, an ester, or "click" reagent such as an alkyne, azide, alkene, hydrazine, hydrazine derivative, alkoxyamine, alkoxyamine derivative, aminoxy, thiol group. Maleimide, isothiocyanate, aldehyde and ester groups efficiently react with peptide thiol-or amine-containing residues (cysteine, lysine) and so a conjugate can easily form. Other bioorthogonal functional groups can be engineered into peptides and proteins for the purpose of conjugating them with alkyne, azide, alkene, hydrazine, aminoxy or thiol groups.

As used herein, the term 'alkyl' refers to straight or branched groups, which unless otherwise specified, contain from 1-10 and suitably from 1-7 carbon atoms. The term 'aryl' refers to aromatic groups which comprise for example phenyl groups, optionally linked to alkyl groups.

Compounds of formula (I) may be prepared using methods described in WO2012/063028.

For example, a compound of formula (II) above is, in general terms, obtainable by linking a group A to either a targeting moiety T or a chelator molecule, and then connected to the other of these. Thus for example, they may be obtained by reacting a compound of formula (III) above, which is reacted with a compound of formula (IV)

T-H (IV)

Where T is as defined above. Suitable reaction conditions will depend upon factors such as the precise nature of the groups A, T etc. and will be determinable to a skilled chemist.

Compounds of formula (III) will themselves be produced by coupling a compound of formula (V)

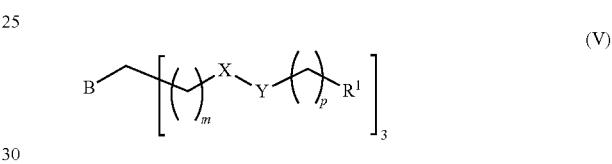

with a reactive group such as a maleimide group, for example as shown in Example 5 of WO2012/063028.

A particular compound of formula (V) where B is a group $H_2N(CH_2)_2C(O)NH$ is shown in Zhou T et al. J. Med Chem. 2006, 49, 4171-4182 (see compound (1) in scheme below). The compound is a derivative of the tris(hydroxypyridinone chelator CP256 (which may also be known as THP) which is of formula

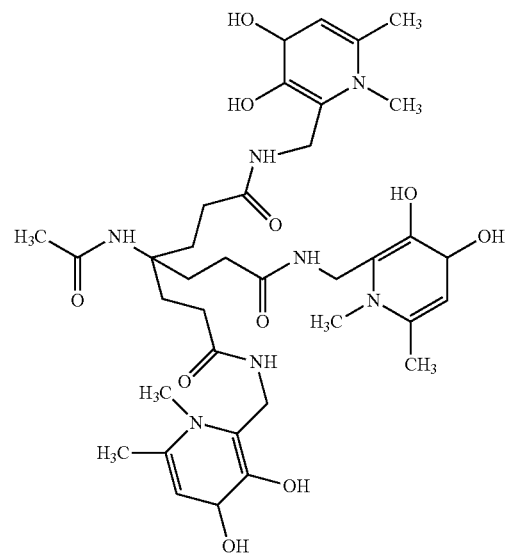 [SMILES: CC(=O)NC(CCC(=O)NCC1=C(O)C(O)C=C(C)N1C)(CCC(=O)NCC1=C(O)C(O)C=C(C)N1C)CCC(=O)NCC1=C(O)C(O)C=C(C)N1C]

CP256.

This may be derivatised as described in WO2012/063028 to form a compound of formula (III) above where A is a maleimide group. Thus a particular compound of formula (III) is of formula YM103 as follows:

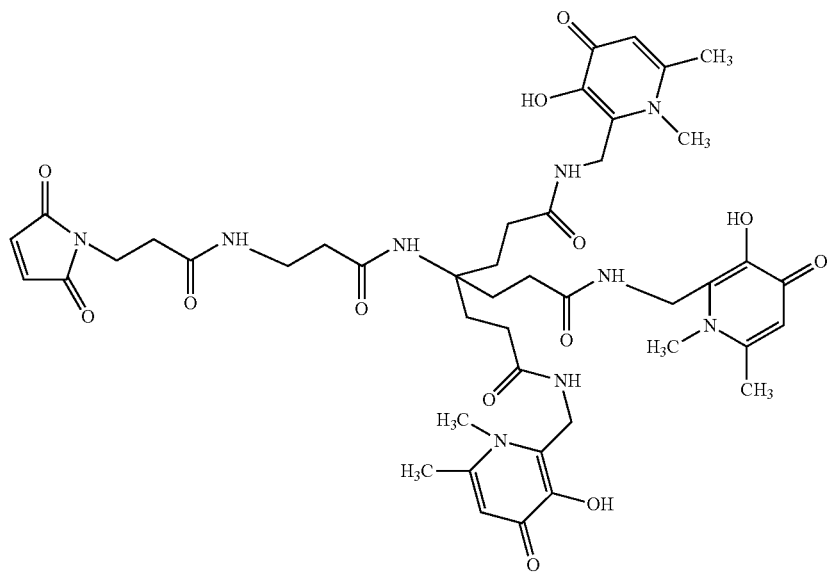 [SMILES: Cc1cc(=O)c(O)c(CNC(=O)CCC(CCC(=O)NCc2c(O)c(=O)cc(C)n2C)(CCC(=O)NCc2c(O)c(=O)cc(C)n2C)NC(=O)CCNC(=O)CCN2C(=O)C=CC2=O)n1C]

of a salt thereof.

An alternative compound of formula III are compounds of formula (I) where A comprises an isothiocyanate group, which is able to conjugate to primary amines.

Examples of such compounds include compounds of formula designated $H_3THP^1$ and $H_3THP^2$ or salts thereof.

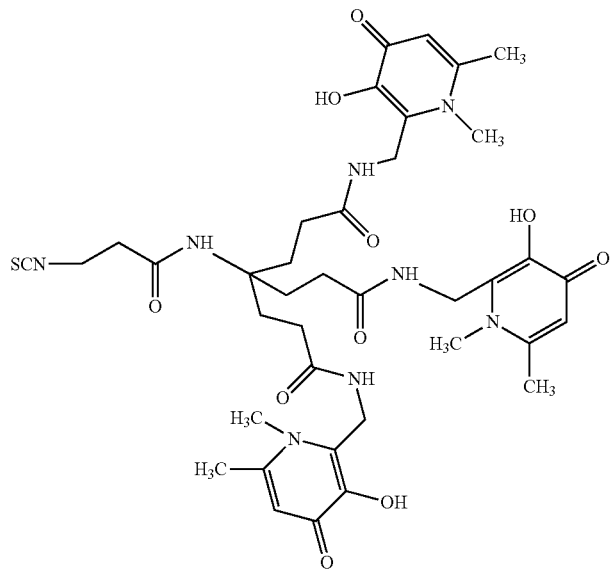

$H_3THP^1$

-continued
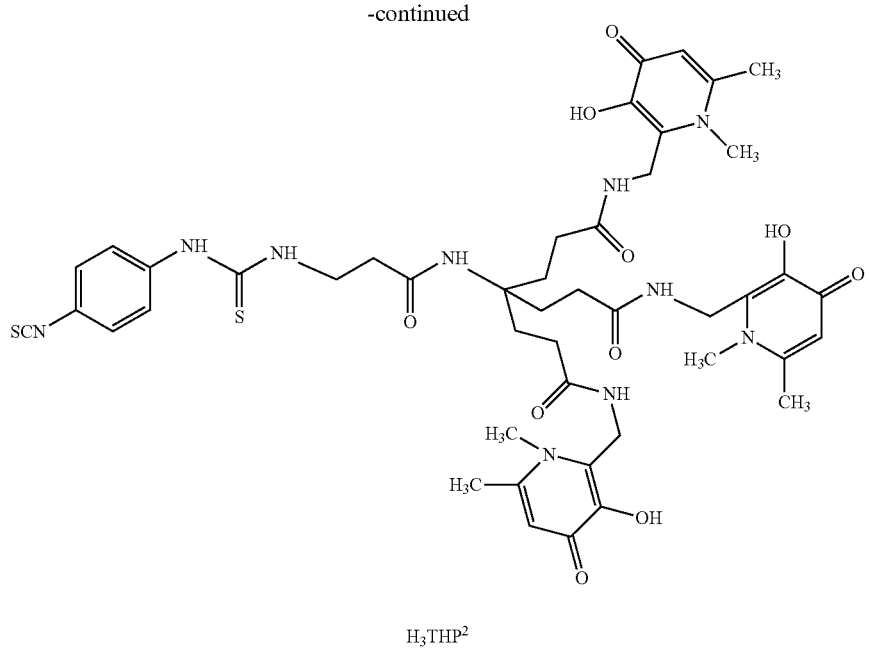
H₃THP²
These compounds may be prepared using methods analogous to those described in WO2012/063028 for example as set out in the following reaction schemes:
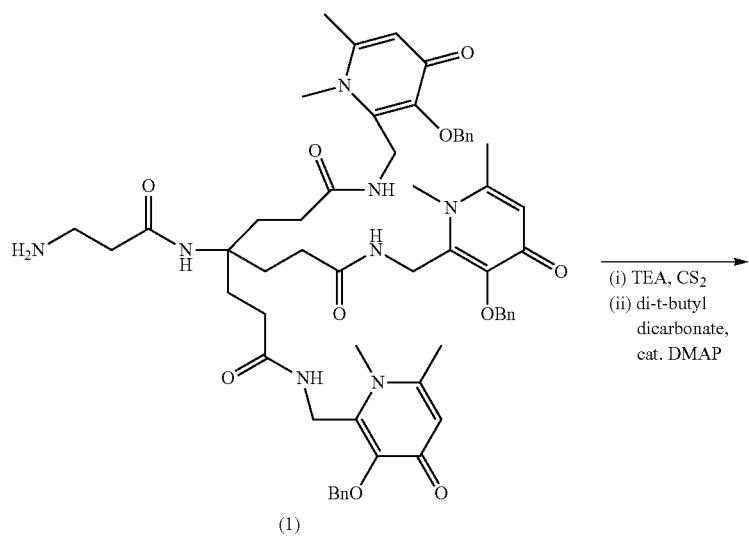
(1)

-continued
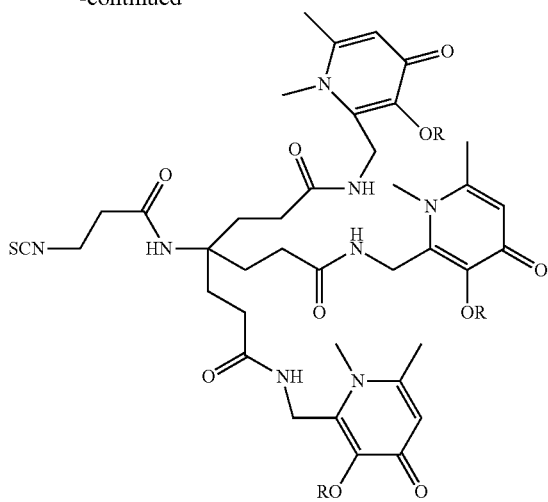
(2) R = Bn     (i) 1M BCl$_3$ in DCM
H$_3$THP$^1$ R = H ← (ii) TFE
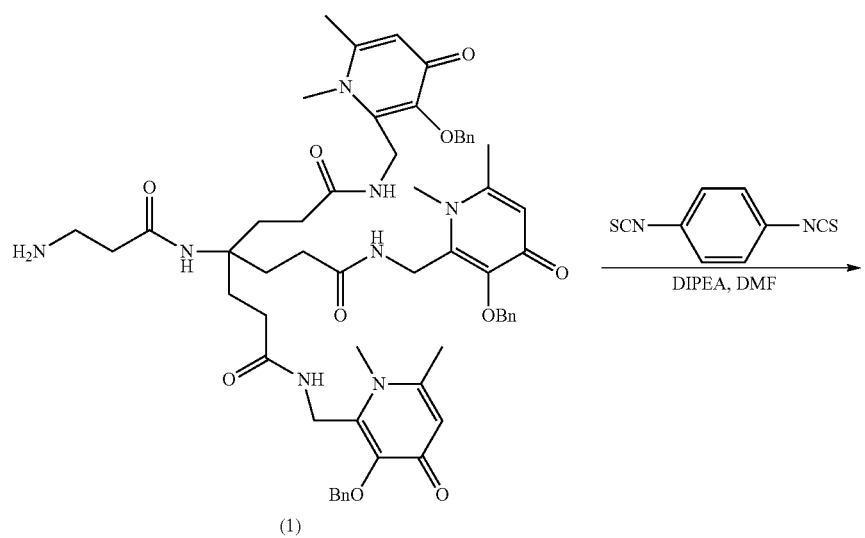
(1)
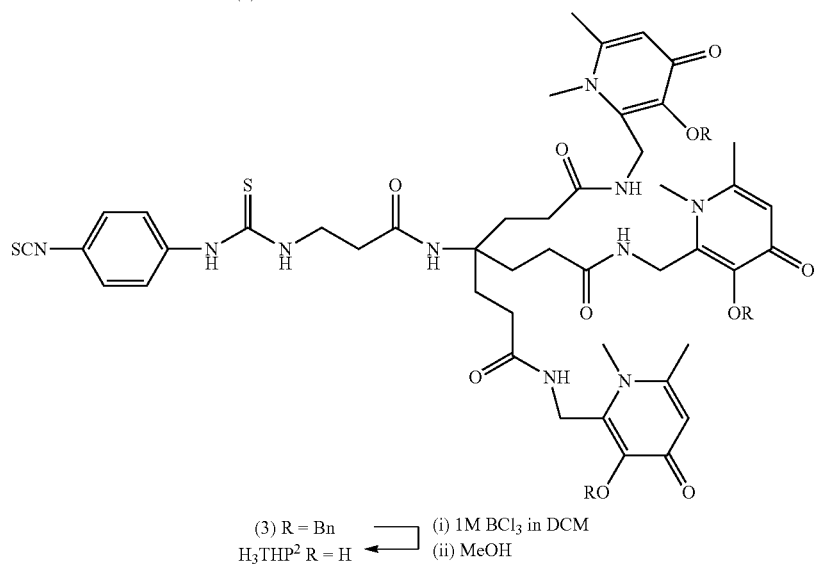
(3) R = Bn     (i) 1M BCl$_3$ in DCM
H$_3$THP$^2$ R = H ← (ii) MeOH In the above scheme, compound (1) as described in Zhou et al. (supra.) is reacted with triethylamine and carbon disulfide in ethanol, to give a precipitated dithiocarbamate intermediate upon addition of water (Munch et al. Tetrahedron Letters (2008), 49, 3117. The precipitated intermediate is re-suspended in a solution of carbon disulfide/ethanol and addition of di-tert-butyl dicarbonate and a catalytic amount of 4-dimethylaminopyridine resulted in formation of (2). Subsequent removal of the benzyl groups with $BCl_3$ in DCM, followed by addition of trifluoroethanol results in $H_3THP^1$, which is purified using reverse phase semi-preparative HPLC to give the product as a trifluoroacetate salt.

To synthesize $H_3THP^2$, an excess of p-phenylene diisothiocyanate and diisopropylethylamine in DMF are added to a solution of (1), followed by isolation of (3) using reverse semi-preparative HPLC. Similar to (2), the benzyl groups of (3) are removed using $BCl_3$ in DCM, followed by addition of methanol, resulting in a chloride salt of bifunctional chelator $H_3THP^2$.

Suitable salts are pharmaceutically acceptable salts such as halide salts and in particular chlorides.

Such compounds have been found to give rise fast radiolabelling (<5 minutes) with $^{68}Ga$, at room temperature and physiological pH. Such pHs can be achieved in the compositions of the invention using material direct from the $^{68}Ga$ generator.

The compositions of the invention may comprise further excipients or pharmaceutically acceptable carriers or fillers as would be understood in the art, as well as reagents such as stabilisers, antimicrobial agents, cryoprotectants, antioxidants, free radical scavengers, solubilizing agents, tonicifying agents, surfactants and collapse temperature modifiers, used in lyophilisation.

Suitable fillers for use in the formulations include for example, sugars such as mannitol, lactose, sucrose, trehalose, sorbitol, glucose, or raffinose, or amino acids such as arginine, glycine or histidine, as well as polymers such as dextran or polyethylene glycol (PEG).

Suitable free radical scavengers are those which protect against autoradiolysis, such as ascorbic acid or gentisic acid. The amount of free radical scavenger which may be added to the composition will depend upon factors such as the nature of the scavenger used and the nature of the composition. In a typical embodiment, a kit may contain from 1-4% w/w free radical scavenger.

Tonicifying agents may be selected for example from sodium chloride, sucrose, mannitol or dextrose.

Antimicrobial agents may be selected from benzyl alcohol, phenol, m-cresol, methyl paraben or ethyl paraben.

Surfactants may include polysorbate such as polysorbate 80.

Collapse temperature modifiers may be selected for example, from dextran, hydroxyethyl starch, Ficoll or Gelatin.

In a particular embodiment, the compositions do not include agents which may inhibit metals other than gallium as described in Belgium Patent No. 1021191.

These compositions may be formed into kits for use in a medical imaging procedure and such kits form a further aspect of the invention. Thus the invention further provides a kit for use in a method as described above, said kit comprising a composition comprising a pharmaceutically acceptable buffer and optionally also a pharmaceutically acceptable basic reagent, and a chelator that is able to chelate radioactive gallium within a pH range of from 3 to 8 and at moderate temperature, said chelator being optionally linked to a biological targeting agent. The chelator is in admixture with the buffer composition in the kit. Although they may be provided in the form of solutions, in particular sterile solutions, the components of the kit are suitably in a solid form in particular in lyophilized or freeze-dried form. Each kit suitably comprises sufficient reagents to carry out one or more molecular imaging procedures held within a container. The container is a sterile sealed container and may be filled with an inert atmosphere such as nitrogen gas. Such kits may further comprise elements such as instructions and outer packaging and may be supplied to hospitals or clinics for reconstitution in situ, using a supply of gallium radiolabels present in appropriate generators.

Certain compositions used in these kits are novel and these form a further aspect of the invention. Thus the invention further provides a unitary composition for use in a method described above, said composition comprising (i) a chelator which is able to chelate with a gallium radionuclide at pH 3 to 8 and at moderate temperature, optionally linked to a biological targeting agent, (ii) a pharmaceutically acceptable buffer and optionally also (iii) a pharmaceutically acceptable basic reagent, wherein (ii) and optionally (iii) are present in the composition in amounts sufficient to result in a pH of from 3 to 8 where eluate directly from a gallium generator is added to the composition.

In particular, the gallium radionuclide chelator is a compound of formula (I) as described above. The composition may be in solution, for example in sterile solution, but is suitably in solid form, for example in lyophilized or freeze-dried form.

The composition of the invention is one which, in solution, has pH in the range of from 3 to 8 after addition of acidic gallium solution obtained directly from a gallium generator. It suitably includes a pharmaceutically acceptable buffer as described above, and also a pharmaceutically acceptable basic reagent, also as described above.

In a further aspect, the invention provides a process for producing a composition of the invention as described above, said method comprising mixing a chelator as defined above with a suitable amount of a pharmaceutically acceptable basic buffer and optionally also a pharmaceutically acceptable basic reagent and optionally lyophilising the resultant mixture.

In a particular embodiment, the compositions are prepared by mixing together components as described above in aqueous solution. The solution will suitably comprise the chelator of formula (I) in a concentration in excess of 5 µM for example from 10-100 µM, a base in a concentration from 01.-0.6M and a buffer in a concentration of from 0.01-0.6M, together with fillers and other excipients as described above as required. Thereafter, the composition is suitably subjected to a lyophilisation procedure as would be understood in the art, to produce a dried composition.

The amount of composition subjected to the lyophilisation procedure may be sufficient to produce sufficient for a one or two therapeutic or imaging operation. In such cases, it may be preferable to lyophilise the composition in vials, in particular glass vials. Alternatively, where larger volumes of composition are subjected to drying, the dried composition may be subsequently divided into individual dosage units.

Once produced in this way, the composition may packaged and stored for distribution, ready for reconstitution with an acid gallium solution, such as a $^{68}Ga$ eluate from a radiolabel generator, in situ.

In such generators, $^{68}Ga$ radionuclide is supplied on a column which is eluted with an acid, in particular and inorganic acid such as hydrochloric acid, at concentrations of from 0.05M-1M, for example from 0.05 to 0.6M HCl, in particular at about m 0.1M HCl, to obtain the $^{68}$Ga radionuclide for use in an imaging procedure.

$^{67}$Ga radionuclides, which may be used in molecular imaging or therapy, are generally prepared in a cyclotron procedure, and supplied in the form of an acid salt such as $^{67}$Ga citrate. Solutions produced may be used as the acidic gallium solution in the method of the invention.

In accordance with the invention, the product obtained is directly useable in a physiological procedure such as imaging procedure or therapy since the pH of the eluate is adjusted upwards by the presence of the base and buffer at the same time as the labelling process, in which the radionuclide becomes chelated. The process is rapid and easy to operate with few handling steps. This ensures that the reagent has a good useful life before the half-life of the radionuclide is eroded, with minimal radiation exposure to operators, minimal opportunity for microbial contamination, and minimal requirement for complex and costly equipment.

The amount of eluate that will be added to the reagents will vary depending upon factors such as the precise nature of the eluate and the composition, the required amount of reagent required for the imaging procedure, the size and nature of the patient to whom the composition is to be administered. However, typically, about 3-7 ml for example about 5 ml eluate will be added to produce a suitable dosage unit.

If required, a dried composition of the invention may be rehydrated with sterile water or saline, before addition of eluate, but in a particular embodiment, the eluate is added directly to the dried reagents.

In a further aspect, the invention provides a radiolabelled product obtained by a method as described above for use in a molecular imaging or radionuclide therapy procedure. Suitable molecular imaging procedures are well known in the art and include PET and SPECT procedures as well as X-ray Computed Tomography (CT) and Cerenkov luminescence imaging (CLI).

Thus in a further aspect, the invention provides a method for obtaining a molecular image of a patient, said method comprising carrying out a process to generate a radiolabelled product as described above, administering the product into patient in need thereof and monitoring the results using a molecular imaging technique.

Yet a further aspect provides a method for treating a patient with a radionuclide, said method comprising carrying out a process to generate a $^{67}$Ga radiolabelled product as described above, and administering the product into patient in need thereof.

The amount of radiolabelled product administered will vary depending upon factors such as the nature of the patient and the organ or tissue targeted by the targeting moiety in the composition, the nature of the radiolabel and the particular imaging technique or therapy employed. The precise amount administered will be determined in accordance with usual clinical practice.

Thus the invention provides effective 'cold kits' for use in a range of clinical situations where gallium and in particular $^{68}$Ga is utilised. Physiologically acceptable products may be generated rapidly and easily at room temperature, and so the available half-life of the radiolabel is maximised. The level of labelling (radiochemical purity) using such chelators and in particular, compounds of formula (I) is particularly effective, typically in excess of 95% and therefore, significant purification procedures may be avoided.

BRIEF DESCRIPTION OF THE DRAWINGS

The invention will now be particularly described by way of Example with reference to the accompanying FIGURES in which:

FIG. 1 is a graph showing the results of a comparison of chelation efficiency of a range of chelators using the method of the invention.

However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1

Preparation of $^{68}$Ga Labelled Reagent

A range of compositions comprising the chelator CP256 were prepared containing various concentrations of pharmaceutically acceptable buffer (sodium phosphate buffer) and pharmaceutically acceptable basic reagent (sodium hydroxide) as set out in Table 1 below. The mixtures were lyophilised under vacuum overnight.

An Eckert and Zeigler $^{68}$Ga generator was eluted with 0.1M HCl, to produce 5 ml eluents of 300 MBq per elution. Portions (1 ml) of the eluent were added each of the compositions at room temperature.

The pH of the resultant solutions was measured. The % radiolabelling of the CP256 (THP) was investigated using TLC. The results are also shown in Table 1 below.

TABLE 1

| Reagent(amounts) | | | | |
|---|---|---|---|---|
| CP256 (nmoles) | NaOH (mmoles) | Phosphate buffer mmoles) | pH | Radiolabelling % TLC |
| 13.5 | 0.15 | 0.10 | 7 | >47 |
| 13.5 | 0.10 | 0.10 | 7 | >74 |
| 13.5 | 0.15 | 0.25 | 7 | >76 |
| 13.5 | 0.00 | 0.50 | 4 | >85 |
| 13.5 | 0.10 | 0.25 | 7 | >89 |
| 13.5 | 0.05 | 0.25 | 5-6 | >90 |
| 13.5 | 0 | 0.25 | 4 | >90 |
| 13.5 | 0.05 | 0.10 | 5-6 | >90 |
| 13.5 | 0 | 0.10 | 3-4 | >90 |

The results show that radiolabelled CP256 was obtained with high levels of efficiency in 2 minutes. The high level of purity in some instances would mean that there is no need to further purify the gallium before administration to patients.

Example 2

Preparation of $^{68}$Ga Labelled Reagent

The methodology of Example 1 was repeated using a range of formulations comprising 0.13M sodium bicarbonate, 0.1M phosphate buffer (PBS) and a range of CP256 concentrations as listed in the following Table. Highly efficient labelling was achieved in relation to the concentration of the chelator as illustrated in Tables 2 and 2a.

TABLE 2

| CP256(THP) Concentration μM | % Labelling | Standard Dev |
|---|---|---|
| 1000 | 97.55 | 1.45 |
| 100 | 95.76 | 4.84 |
| 10 | 91.52 | 2.36 |
| 1 | 62.62 | 7.99 |
| 0.1 | 31.29 | 4.47 |
| 0.001 | 0.00 | 1.63 |

TABLE 2A

| CP256(THP) Concentration | % Labelling | Standard Dev |
|---|---|---|
| 1 mM | 97 | 0.15 |
| 500 μM | 9695.76 | 1.42 |
| 50 μM | 9791.52 | 0.97 |
| 5 μM | 9762.62 | 0.06 |
| 500 nM | 981.29 | 0.14 |
| 50 nM | 150.00 | 3.10 |

Example 3

Comparison of Radiolabelling Using Different Chelators

The method of Example 1 was repeated using a range of different chelators (DOTA, NOTA, TRAP, NOTP, HBED, DFO and THP) at various concentrations. The amounts of phosphate buffer and sodium hydroxide was adjusted to provide a pH of either 4 or 7 on addition of the 0.1M eluate. Solutions were incubated at room temperature for 10 minutes.

The results at pH 7 are shown in FIG. 1. Acceptable labelling efficiencies in excess of 95% were only found with with THP and DFO. All other chelators did not label >95% at pH 7.0. In addition the concentration of most the other chelators had to be quite high to achieve >90% labelling Example 4

Lyophilised Kit

A vial comprising a lyophilised reagent mixture, prepared as described above and comprising CP256(THP)(40 μg) linked to a PSMA targeting agent (30 nmoles), sodium bicarbonate (42 mg), sodium phosphate monobasic anhydrous (8.2 mg) and sodium phosphate dibasic heptahydrate (8.5 mg) is prepared. It could be reconstituted using a 0.1M HCl eluate (5 ml) obtained from an Eckert and Zeigler $^{68}$Ga generator to produce a solution of pH 6.5 to 7.0, which may be used in therapy or in molecular imaging.

Example 5

Alternative Lyophilised Kit

A vial comprising a lyophilised reagent mixture as described in Example 4 but also containing from 1 to 2 mg ascorbic acid may also be prepared. This kit also can be reconstituted using a 0.1M HCl eluate (5 ml) obtained from an Eckert and Zeigler $^{68}$Ga generator to produce a solution of pH 6.5 to 7.0, which may be used in therapy or in molecular imaging.

The invention claimed is:

1. A method for preparing a complex comprising a radioisotope of gallium for use in radiotherapy or in a medical imaging procedure, said method comprising adding a gallium radioisotope eluate obtained directly from a gallium radionuclide generator without additional purification or concentration steps to a chelator composition comprising a pharmaceutically acceptable buffer in amounts sufficient to increase the pH to a level in the range of 3 to 8, and a chelator that is able to chelate radioactive gallium within said pH range and at a temperature of 10 to 30 °C., said chelator being linked to a biological targeting agent, wherein said chelator is selected from desferrioxamine-B (DFO), bis(2-hydroxybenzyl)ethylenediaminediacetic acid (HBED), 1,4,7-triazacyclononane macrocycle substituted with phosphonic groups at the amines (NOTP), or a compound of formula (I)

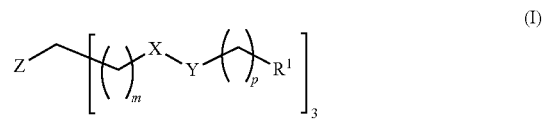

(I)

or a salt thereof; wherein one of X and Y is C=O and the other is NR; wherein each m and p are independently selected from 0 to 6; wherein $R^1$ is a chelating group capable of chelating a radionuclide and is selected from:

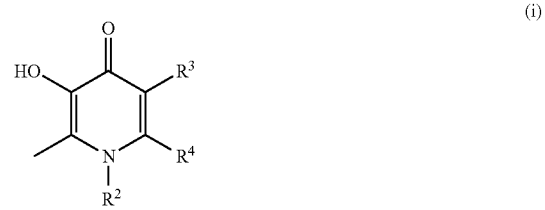

(i)

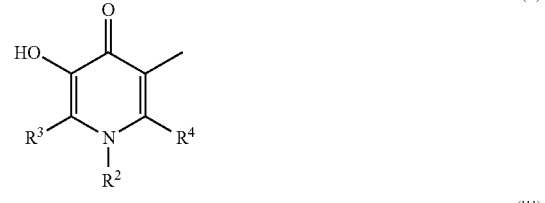

(ii)

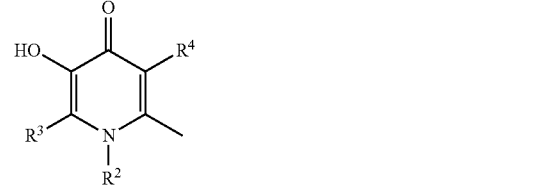

(iii)

wherein R, $R^2$, $R^3$ and $R^4$ independently hydrogen or an optionally substituted $C_{1-7}$alkyl group; and where Z is hydrogen or a group of formula —B'—H, —B'-A, or a group —B'-A*-T, where T is a targeting group capable of binding to a target of interest in a subject;

A is a reactive group allowing coupling to the group T,

A* is a reacted reactive group A;

B' is a linker group for linking the chelating group to a reactive group A, and is represented by the formula:

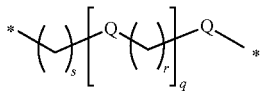

(iv)

wherein each Q is independently selected from a group consisting of —NR$^5$—, —C(O)NR$^5$—, —C(O)O, —NR$^5$C(O)NR$^5$—, —NR$^5$C(S)NR$^5$— and —O—, each R$^5$ is independently hydrogen or an optionally substituted C$_{1-7}$ alkyl group, each q and s are independently selected from 0 to 6 and each r is independently selected from 1 to 6, wherein said chelator, buffer are in lyophilized or freeze-dried form, and wherein said chelator composition does not include agents inhibiting metals other than gallium.

2. The method of claim 1, wherein the gallium radioisotope eluate is at a pH of less than 2.

3. The method of claim 1, wherein the composition further comprises a pharmaceutically acceptable basic reagent selected from sodium hydroxide, potassium hydroxide, a carbonate and bicarbonate.

4. The method of claim 1, wherein the chelator is linked to a biological targeting agent that targets a cancer specific marker.

5. The method of claim 1, wherein the pharmaceutically acceptable buffer is a phosphate buffer, bicarbonate or carbonate buffer, succinate buffer, borate buffer, cacodylate buffer, citrate buffer, a zwitterionic buffer, a tris(hydroxymethyl)aminomethane (TRIS) buffer, morpholine propanesulphonic acid (MOPS), N-(2-hydroxyethyl) piperazine-N'(2-ethanesulfonic acid) (HEPES), tartaric add, arginine or an acetate buffer.

6. The method of claim 4, wherein the cancer specific marker is prostate specific membrane antigen (PSMA).

7. The method of claim 1, wherein the gallium radioisotope eluate is obtained by eluting a $^{68}$Ga radionuclide column with an inorganic acid.

* * * * *